United States Patent [19]

Nodelman

[11] 4,332,936

[45] Jun. 1, 1982

[54] METHOD OF MAKING POLYETHER POLYOLS FROM SOLID HYDROXYL CONTAINING INITIATORS

[75] Inventor: Neil H. Nodelman, New Martinsville, W. Va.

[73] Assignee: Mobay Chemical Corporation, Pittsburgh, Pa.

[21] Appl. No.: 952,019

[22] Filed: Oct. 16, 1978

[51] Int. Cl.$^3$ .................. C07C 41/00; C07H 15/04
[52] U.S. Cl. ................................. 536/120; 536/18.3
[58] Field of Search ............................................ 536/120

[56] References Cited

U.S. PATENT DOCUMENTS

| | | | |
|---|---|---|---|
| 2,902,478 | 9/1959 | Anderson | 536/120 |
| 3,222,357 | 12/1965 | Wismer et al. | 536/120 |
| 3,317,508 | 5/1967 | Winquist et al. | 536/120 |
| 3,346,557 | 10/1967 | Patton et al. | 536/120 |
| 3,357,970 | 12/1967 | Uhyatt et al. | 536/120 |
| 3,433,751 | 3/1969 | Yotsuzuka et al. | 536/120 |
| 3,941,769 | 3/1976 | Maassen et al. | 536/120 |

FOREIGN PATENT DOCUMENTS 37373 3/1965 German Democratic Rep.

*Primary Examiner*—Blondel Hazel
*Attorney, Agent, or Firm*—Gene Harsh; Joseph C. Gil

[57] ABSTRACT

This invention provides a novel method for making polyether polyols from solid initiator compounds containing from 4 to 8 hydroxyl groups. The method involves dissolving the solid initiator compound in a solvent such as dimethyl formamide prior to alkoxylation. The method is particularly useful in making high functional sucrose-based polyether polyols which can be readily processed at moderate temperatures and give low color products. These polyols are particularly suited for the production of rigid polyurethane foams.

1 Claim, No Drawings

METHOD OF MAKING POLYETHER POLYOLS FROM SOLID HYDROXYL CONTAINING INITIATORS

This invention relates to a novel method of making polyether polyols from solid initiator compounds containing from about 4 to about 8 hydroxyl groups. The method involves mixing the solid initiator compound with a compound such as dimethyl formamide prior to alkoxylation. This method is particularly useful in making high functional sucrose-based polyether polyols. Such polyols are useful in preparing polyurethanes, especially polyurethane foams.

BACKGROUND OF THE INVENTION

There is a large amount of art relating to the production of sucrose polyols and other polyols produced with solid initiators. The process most commonly employed is described in U.S. Pat. No. 3,085,085 where sucrose is dissolved in water with an oxyalkylation catalyst such as potassium hydroxide. Alkylene oxide is added over a period of time until the reaction product is a liquid. At this stage the water is removed. The remaining alkylene oxide is then added until the desired polyether polyol is obtained. This method of making sucrose polyols has been found to be satisfactory for many purposes. However, the water present during the initial alkoxylation will react to some extent with the alkylene oxide to form bifunctional by-products. Because of the low equivalent weight of water, even small amounts of water reacting under these conditions will severely reduce the functionality of the resulting polyol. High functionality of sucrose polyols is required to enhance the dimensional stability of rigid polyurethane foams made with such polyols.

Severe problems arise when water cannot be used as a solvent for high melting sucrose. Normally, solid polyols such as sucrose undergo partial decomposition as they melt and these solid compounds are insoluble in any oxyalkylation-resistant solvents. Prior art in this regard is discussed e.g. in U.S. Pat. Nos. 3,190,927 and 3,346,557. In these patents a solution is given as to how to get sucrose into a form in which it can be alkoxylated. An adduct of the high melting polyol with 1 to 4 mols of an alkylene oxide is disclosed as a suitable solvent for the full alkoxylation process. The disadvantage of this process is that it must be carried out in two stages. A similar process is disclosed in U.S. Pat. No. 3,357,970.

In U.S. Pat. No. 3,442,888 the sucrose is mixed with a substantial amount of glycerol and an alkali metal hydroxide catalyst. These polyols, however, also suffer from the fact that glycerol, with a functionality of only three, must be used in large amounts. The products are inevitably low functional sucrose polyols.

In U.S. Pat. No. 3,640,997 sucrose is mixed with specific amounts of low functional ethylene diamine and a specific amount of an alkali metal hydroxide catalyst. The patent specifically discloses a lower limit of 0.6 mols of ethylene diamine which can be used per mol of sucrose. Less than this amount creates solubility problems. The sucrose cannot completely react and will precipitate out of the polyol. The use of at least 0.6 mols of ethylene diamine per mol of sucrose places an upper limit on the functionality of the polyol produced. The highest functional polyol in the examples of the patent is 5.6.

In U.S. Pat. No. 3,856,806 solid hydroxyl-containing initiators and a tertiary amine catalyst are directly alkoxylated with a blend of ethylene oxide and vicinal alkylene oxide having 3 to 4 carbon atoms. The process requires the blending of alkylene oxides.

In U.S. Pat. No. 3,941,769 sucrose is added to an inert aromatic hydrocarbon solvent such as toluene. Specific amounts of a short chain polyol, monoamine or polyamine, a small quantity of water, and a small amount of alkali metal hydroxide catalyst are added to the suspension followed by alkoxylation. High functional polyols can be produced by this method, i.e. with a functionality of 7 or more. However, polyols with a functionality of more than about 6.5 can only be obtained at the expense of cutting the alkoxylation short, i.e., stopping the alkoxylation before the OH number is reduced below about 400. Each polyol produced in the reference which has an OH number below 400 also has a functionality of significantly less than 6.5. Example 4 shows a polyol with a functionality of 7.18 but a hydroxyl number of 519 and viscosity of 400,000 cP. Polyols with viscosities in such a range cannot be easily handled by conventional foaming equipment. The viscosity can only be lowered as the alkoxylation proceeds and the OH number is lowered. The functionality of the resulting polyol would be significantly reduced as the alkoxylation continues because more and more water will react, forming difunctional polyols.

Most of the peculiar problems associated with making polyether polyols from solid initiators compounds containing hydroxyl groups stem from the fact that these compounds will not dissolve in typical solvents. The art has esssentially been led in the various directions mentioned above to circumvent this problem, a problem which is described in an early patent, U.S. Pat. No. 2,902,473 as follows—". . . no practical solvent is known that will simultaneously dissolve these polyols, the alkylene oxides and the conventional caustic alkali catalysts without entering into reaction with the oxide" (column 1, lines 27-30).

DESCRIPTION OF THE INVENTION

It has now been surprisingly discovered that dimethyl formamide and other closely structurally related compounds when mixed with solid initiators permit the alkoxylation of solid initiator compounds to proceed at a rapid pace, particularly in the presence of a co-initiator and amine catalyst or an amine functional co-initiator which acts as both catalyst and co-initiator. Even though dimethylformamide is known as a solvent for sucrose in other chemical areas and even though dimethylformamide is known as an acceptable reaction medium for the production of linear polyesters from aromatic dicarboxylic acids and alkylene oxides (e.g. U.S. Pat. No. 2,901,505), it has never been recognized for solving the solubility problems of reacting alkylene oxides with solid initiator compounds containing hydroxyl groups to produce polyether polyols. Moreover, the use of dimethylformamide has been found to be particularly useful in the production of high functional sucrose based polyether polyols.

Thus, the present invention relates to a process for making polyether polyols wherein a solid initiator compound containing from 4 to 8 hydroxyl groups is mixed with a solvent corresponding to the formula

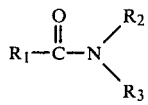

wherein

R₁ is H or C₁–C₃ alkyl, preferably H or —CH₃, and most preferably H;

R₂ and R₃ may be the same or different and represent C₁–C₃ alkyl, and preferably C₁ and wherein R₁ and either R₂ or R₃ may together form a cyclic ring.

The initiator/solvent mixture is then alkoxylated in the presence of a catalyst, preferably in the presence of an amine catalyst and co-initiator or an amine functional co-initiator which acts as both catalyst and co-initiator.

Suitable solid initiator compounds containing from 4 to 8 hydroxyl groups include sucrose, α-methyl glucoside, pentaerythritols, sorbitol, mannitol, di- and polyglycerols, glycolized starch, inositol and the like. Mixtures of these compounds may also be used. Sucrose is the preferred solid initiator because of its high functionality and low price. High functional sucrose polyols can be prepared from sucrose which have excellent dimensional stability at both high and low temperatures.

The solvent used in the present invention, i.e. the solvent of the general formula mentioned above, is a partial solvent for the solid initiator compound and otherwise functions as a slurrying medium. These solvents are generally classified as aprotic solvents with moderately high dielectric constants. Suitable specific solvents of this type include dimethyl formamide, dimethyl acetamide, N-methyl pyrrolidone and the like. These named compounds are generally readily available. However, any compounds of the above-mentioned general formula would be suitable. Dimethyl formamide is preferred. The solvent may be used in amounts ranging from about 5 to about 70 parts by weight based on 100 parts of solid initiator. While amounts exceeding this upper limit could be used, unnecessary amounts are undesirable because the solvent must generally be removed at the end of the reaction via distillation.

Any aromatic hydrocarbon solvent which is inert under the reaction conditions and has a boiling point in the range of from about 80° to 180° C. may be used in addition to the above noted aprotic solvent. Such solvents include toluene, xylene, benzene, chlorobenzenes, ethyl benzene and the like. Toluene is preferred. These solvents may also be mixed with aliphatic solvents with comparable boiling points. There is essentially no upper limit to the amount of hydrocarbon solvent which can be used. However, as with the aprotic solvent, it is advisable to minimize the amount used since the solvent eventually has to be removed from the final product. Sufficient solvents (including aprotic solvent) should be used to provide a good slurrying media for the solid initiator. Generally the total amount of solvent (i.e. both aprotic and hydrocarbon solvents) ranges from 5 to 70 parts by weight of solvent per 100 parts solid initiator used.

The reaction is best carried out in the presence of an amine catalyst and co-initiator or a co-initiator which acts as both a catalyst and co-initiator. Such catalysts which promote alkoxylation reactions are known. They include, for example, trimethylamine, triethylamine, tetramethylbutanediamine, diethyl methyl amine, dimethyl amine, diethyl amine, tri-n-propyl-amine, pyrrolidine, piperidine, 4-methyl piperidine, N-methyl piperidine, N-ethyl piperidine, piperazine, N-methyl piperazine, triethylene diamine, tetramethyl guanidine, triethanolamine, mono-, di- or tri-isopropanolamine, N-methyl-diethanolamine, N-ethyl diethanolamine, ethylene diamine, diethylene triamine, triethylene tetramine and the like.

Many of these amine catalysts act as co-initiators as well. Examples of such amine functional co-initiators include triethanolamine, diethylene triamine, tri-ethylene tetramine and the like.

The amine catalysts should be used in amounts ranging from 0.2 to 4 parts, and preferably 0.4 to 2 parts by weight based on 100 parts by weight of solid initiator. For amine co-initiators larger quantities should generally be used. At least 3 parts by weight based on 100 parts by weight of solid initiator is desirable. There is no theoretical upper limit to the amount which can be used. However, the functionality of the final polyol is lowered as the amount of co-initiator used is increased.

Co-initiators to be used with the amine catalysts include those lower molecular diols, triols, polyols (and di-, tri- and polyamines) known in the art. These include ethylene glycol, propylene glycol, butane 1,4-diol diethylene glycol, dipropylene glycol, trimethylol propane, glycerol and the like. In general, at least 3 parts by weight of co-initiator is used per 100 parts by weight of solid initiator. Again, there is theoretically no upper limit on the amount of co-initiator to be used. Of course, as the amount increases, the functionality of the final product will decrease.

The reaction could also be carried out in the presence of an alkali metal hydroxide as catalyst, e.g. sodium or potassium hydroxide. However, the use of an alkali metal hydroxide catalyst is neither necessary nor advantageous as discussed below.

The present process can be carried out with up to about 1.3 parts by weight of water based on 100 parts by weight of solid initiator. At least trace amounts of water seem to be necessary for the alkoxylation reaction. The precise reason for this is not known but it is possible that the water has a catalytic effect in helping to open the alkylene oxide ring and thus speed the alkoxylation reaction. Trace amounts of water are normally found in commercial grades of the reactants of the present process, particularly in the sucrose or other solid initiator which will readily absorb moisture from the air. Accordingly, trace amounts are desirable and need not be removed. As an upper limit on the amount of water desired in the reaction mixture, it must be kept in mind that even small amounts of water have a significant effect on lowering the final functionality of the resulting polyol. Thus, large amounts and certainly amounts in excess of 1.3 parts by weight of water are undesirable since high functionality in the final product is generally desired.

Suitable alkylene oxides include any of those known in the art. These include ethylene oxide, 1,2-propylene oxide, 1,2-butylene oxide and 2,3-butylene oxide and the like. Preferred, however, are ethylene oxide and propylene oxide, and most preferably in the sequence discussed below. The amount of oxide used depends on the desired length of the chains extending from the solid initiator, i.e. the desired OH number. (In general, OH numbers of less than 550, and preferably less than 400, are desired.) Because of the small amounts of water used, the alkoxylation reaction can continue indefinitely without reduction of the functionality of the final product and accordingly, there is theoretically no lower limit for the OH number. The functionality of the polyol should not substantially decrease as the alkoxylation proceeds. In general, it is desired to use alkylene oxide in amounts sufficient to give an OH number in the range of from 300–550, and preferably 300–400, with viscosities at 25° C. of from 15,000 to 40,000 mPa.s, and preferably 20–30,000 mPa.s.

A preferred embodiment of the invention is to add ethylene oxide in an amount of from about 0 to 15% of the total alkylene oxides used at the beginning of the alkoxylation. The alkoxylation is then completed with propylene oxide. This initial ethylene oxide charge tends to preserve both the strength and duration of the catalytic activity of any amines which contain active hydrogen atoms. This is apparently due to the fact that the nitrogen atoms of the amine catalyst are not severely hindered with ethylene oxide addition as they would be with propylene oxide and other higher molecular weight oxides. Thus, it is best to add at least as much ethylene oxide as is necessary to react with all the active hydrogen atoms, if any, of the amine catalyst, prior to the use of other alkylene oxides.

The most advantageous method of carrying out the reaction is to add the water (if desired and/or necessary), amine catalyst (if desired), the aprotic solvent and aromatic hydrocarbon solvent or mixture of solvents and the co-initiator to the reactor at ambient temperatures and then add the solid initiator at once with stirring. The mixture is then heated to the desired alkoxylation reaction temperature. A nitrogen pressure of anywhere from about 15 psig to 200 psig, preferably 25 to 140 psig, and most preferably about 2 atmospheres, is then built up in the reactor. The reaction of the alkylene oxide is done under typical conditions for making polyether polyols, i.e., at a temperature of from about 70° C. to 160° C., and preferably 80° C. to 120° C.

When the alkylene oxide addition is complete the polymer is neutralized if an alkali metal hydroxide catalyst is used. The remaining water, aprotic solvent and hydrocarbon solvent are distilled off, i.e. at higher temperatures, under vacuum. The salts produced by the neutralization are removed by filtration by known methods.

There are a number of remarkable features about the processing when the solvents of the present invention, such as dimethylformamide are used.

1. The use of the aprotic solvent allows for the use of an amine catalyst for the alkoxylation reaction to the exclusion of alkali metal hydroxide catalysts such as potassium hydroxide. In typical reactions producing polyether polyols, amine catalysts are insufficient to maintain reaction kinetics for the duration of the reaction. The amine tends to become inactive towards the end of the reaction. For this reason, catalysts such as potassium hydroxide are generally employed even though they must be used as solutions in water. The water is not generally desirable in the reaction mixture because salts are formed requiring both a neutralization and filtration step. The amine catalysts also tend to impart "activity" to the polyol, i.e. at its more reactive with isocyanates than those polyols made without amine catalysis. When solvents such as dimethylformamide are present during the reaction, it has been found that not only does the reaction maintain a constant rate using amine catalysis but the reaction actually speeds up rather than slows down towards the end of the reaction. When nitrogen content analysis of the final product after solvent removal is compared to the amount of nitrogen initially placed in the reactor (i.e. from the amine catalyst), it is found that there is a higher amount of nitrogen at the end of the reaction than at the start. This leads to the conclusion that a small portion of the aprotic solvent is reacting in some manner to form active amine catalysts during the latter stages of the reaction. This was a completely unexpected and beneficial aspect of the use of the aprotic solvents. The alkoxylation reaction is smooth and faster than expected.

2. The reaction in the aprotic solvent also proceeds very quickly at temperatures as low as 80° C. In the absence of such a solvent, the reaction will generally not proceed at sufficiently high rates at low temperatures using normal amounts of catalyst.

3. It has been found that the ability to carry out the reaction at 80° C. enables the production of a product with consistently low color, e.g. a Gardner color in the 2–3 range. Low color polyol is very important in a number of applications where white polyurethane foam is required for aesthetic reasons.

The polyols produced by the above-described process are useful as starting components in the preparation of polyurethanes, particularly rigid polyurethane foams which have good dimensional stability, particularly at low temperatures. The present polyols also have good activity when used as a polyol in a polyurethane foaming reaction because of the use of the amine catalyst or amine co-initiator and the aprotic solvent derived amines, i.e. foaming reactions using the polyols prepared by the present process exhibit significantly reduced gellation and tack-free times.

Means for making rigid and other polyurethane foams from polyisocyanates, polyether polyols, catalysts, water and/or other blowing agents, e.g. Freon, stabilizers and other additives are well known.

The invention is further illustrated, but is not intended to be limited by the following examples in which all parts and percentages are by weight unless otherwise specified.

EXAMPLES

EXAMPLE 1

A polyether polyol was prepared from the following components:

| Sucrose | 100 | parts by weight |
|---|---|---|
| Glycerol (99%) | 4.55 | |
| Dimethylformamide | 18.84 | |
| Toluene | 18.84 | |
| Triethylamine | 2.83 | |
| Ethylene oxide | 27.22 | |
| Propylene oxide | 244.96 | |

The sucrose, glycerol, dimethylformamide and toluene were added to the reaction vessel with vigorous stirring. This mixture was heated to 80° C. and the reaction vessel then evacuated of air and replaced with a nitrogen atmosphere. The triethylamine catalyst was then added to the reaction mixture and a nitrogen pressure of 30 psig placed on the reactor. The mixture was then heated to 80° C. The ethylene oxide was charged first, followed by the propylene oxide. The oxides were charged at such a rate that the batch temperature remained constant at 80° C. with external heating. When the desired OH number was reached, the propylene oxide charge was stopped. The batch was then stripped, at elevated temperature, of the dimethylformamide and toluene.

The product polyol had the following properties:

| | |
|---|---|
| Viscosity (25° C.) | 17,100 cps |
| Color (Gardner) | 2 |
| OH number | 331 |
| Functionality (based on sucrose, glycerine and trace amounts of water) | 7.26 |

EXAMPLE 2

A polyether polyol was prepared from the following components:

| | | |
|---|---|---|
| Sucrose | 100 | parts by weight |
| Glycerol (99%) | 4.55 | |
| Dimethylformamide | 19.66 | |
| Toluene | 19.66 | |
| Triethylamine | 0.42 | |
| Water | 0.20 | |
| Ethylene oxide | 28.81 | |
| Propylene oxide | 259.29 | |

The reaction procedure was substantially similar to Example 1. The final polyol had the following properties:

| | |
|---|---|
| Viscosity (25° C.) | 21,400 cps |
| Color (Gardner) | 2 |
| OH number | 365 |
| Functionality (based on sucrose, glycerine and water) | 7.10 |

EXAMPLE 3

A polyether polyol was prepared from the following components:

| | | |
|---|---|---|
| Sucrose | 100 | parts by weight |
| Glycerol | 4.55 | |
| Dimethylformamide | 19.66 | |
| Toluene | 19.66 | |
| Triethylamine | 0.42 | |
| Water | 0.20 | |
| Ethylene oxide | 4.75 | |
| Propylene oxide | 283.35 | |

The reaction procedure was substantially similar to Example 1. The final polyol had the following properties:

| | |
|---|---|
| Viscosity (25° C.) | 21,600 cps |
| Color | 3 |
| OH number | 360 |
| Functionality (based on sucrose, glycerol and water) | 7.10 |

EXAMPLE 4

A polyether polyol was prepared from the following components:

| | | |
|---|---|---|
| Sucrose | 100 | parts by weight |
| Diethylene triamine (DETA) | 9.52 | |
| Water | 0.85 | |
| Dimethylformamide | 21.21 | |
| Toluene | 21.21 | |
| Ethylene oxide | 31.48 | |
| Propylene oxide | 283.29 | |

A procedure similar to that of Example 1 was used except the reaction temperature was 105° C. The final polyol had the following properties:

| | |
|---|---|
| Viscosity (25° C.) | 19,900 cps |
| OH number | 380 |
| Functionality (based on sucrose, DETA, water) | 6.70 |

EXAMPLE 5

A polyether polyol was prepared from the following components:

| | | |
|---|---|---|
| Sucrose | 100 | parts by weight |
| Triethanolamine (TEOA) | 7.63 | |
| Dimethylformamide | 19.61 | |
| Toluene | 19.61 | |
| Water | 0.78 | |
| Ethylene oxide | 28.04 | |
| Propylene oxide | 252.41 | |

The procedure was similar to Example 1 except that the reaction temperature was 105° C. The final polyol had the following properties:

| | |
|---|---|
| Viscosity | 15,000 cps |
| OH number | 383 |
| Functionality (based on sucrose, glycerol and water) | 6.66 |

EXAMPLE 6 (Comparison)

A polyether polyol was prepared from the following components which did not include the aprotic solvent:

| | | |
|---|---|---|
| Sucrose | 100 | parts by weight |
| Toluene | 75.34 | |
| Glycerine (99%) | 4.55 | |
| Triethylamine | 2.83 | |
| Ethylene oxide | 27.22 | |
| Propylene oxide | 244.96 | |
| Potassium hydroxide | 1.88 | |

The reaction procedure was similar to Example 1. However, due to the lack of the aprotic solvent, the reaction became very sluggish. Potassium hydroxide had to be added towards the end of the reaction to bring the product to an acceptable OH value. The final product had the following properties:

| | |
|---|---|
| Viscosity (25° C.) | 27,300 cps |
| OH number | 366 |
| Color (Gardner) | 6 |
| Functionality (based on Sucrose, glycerine and | |

| | -continued | |
|---|---|---|
| water) | 7.26 | |

EXAMPLES 7-9

Excellent rigid polyurethane foams were prepared from the polyols prepared in Examples 1, 4 and 5.

| Example | 7 | 8 | 9 |
|---|---|---|---|
| Polyol from Example 1 | 100.0 | — | — |
| Polyol from Example 4 | — | 100.0 | — |
| Polyol from Example 5 | — | — | 100.0 |
| DC-193[1] | 1.5 | 1.5 | 1.5 |
| Dabco R-8020[2] | 1.0 | 1.0 | 1.0 |
| R-11-B[3] | 35.0 | 35.0 | 35.0 |
| Isocyanate[4] (1.05 Index) | 84.1 | 96.3 | 97.0 |
| Reactivity | | | |
| Mix Time (secs)[5] | 10 | 10 | 10 |
| Cream (secs)[6] | 35 | 25 | 30 |
| Gel (secs)[7] | 105 | 85 | 85 |
| Tack free (secs)[8] | 130 | 105 | 115 |
| Rise (secs)[9] | 190 | 135 | 140 |

[1]DC-193 is a polysiloxane surfactant foam Dow-Corning for use in rigid foams.
[2]Dabco R-8020 is a triethylenediamine catalyst from Air Products Corp.
[3]R-11-B is monofluorotrichloro methane.
[4]The isocyanate used was a polymethylene polyphenyl isocyanate with an NCO content of 31.5% and an average functionality of 2.6–2.7.
[5]Mix Time: the duration of mixing after the isocyanate is added to the resin blend.
[6]Cream Time: the elapsed time from the start of mix time until the time at which a change in color of the mixed liquid from brown to creamy tan is noted.
[7]Gel Time: the elapsed time from the start of mix time until the time at which a ⅛" diameter applicator stick inserted 2" into the rising foams, pulls with it a 6" long "string" when it is quickly removed from the foam.
[8]Tack Free Time: the elapsed time from the start of mix time until the time at which a clean dry tongue depressor lightly touched to the foam surface can be removed without pulling off the foam surface.
[9]Rise Time: the elapsed time from the start of mix time until the time at which no additional visible foam rise can be observed.

What is claimed is:

1. In a process for making a polyether polyol wherein a solid initiator compound containing from 4 to 8 hydroxyl groups is reacted with an alkylene oxide in the presence of an amine catalyst or an amine functional coinitiator which functions as a catalyst, the improvement which comprises mixing and partially dissolving the solid initiator in from about 5 to about 70 parts by weight, based on 100 parts by weight of solid initiator of dimethylformamide.

* * * * *